United States Patent [19]

Morin et al.

[11] Patent Number: 4,549,584

[45] Date of Patent: Oct. 29, 1985

[54] PROCESS AND DEVICE FOR FILLING CHROMATOGRAPHY COLUMNS

[75] Inventors: Daniel Morin, Orthez; Roland Prechner, Pau, both of France

[73] Assignee: Societe Nationale Elf Aquitaine (Production), Courbevoie, France

[21] Appl. No.: 539,113

[22] Filed: Oct. 5, 1983

[30] Foreign Application Priority Data

Oct. 5, 1982 [FR] France .................................. 82 16672

[51] Int. Cl.[4] .......................... B01D 15/08; B65B 1/24
[52] U.S. Cl. ...................................... 141/73; 141/12; 141/72; 55/386; 210/656; 210/198.2
[58] Field of Search .................... 141/1, 9, 10, 11, 12, 141/69, 71–75, 77–81, 98, 392, 280; 210/656, 198.2; 55/67, 386

[56] References Cited

U.S. PATENT DOCUMENTS

| | | | |
|---|---|---|---|
| 2,998,036 | 8/1961 | Strasheim et al. | 141/72 |
| 3,300,849 | 1/1967 | Wiseman | 141/12 X |
| 3,398,512 | 8/1968 | Perkins, Jr. et al. | 55/386 |
| 3,440,864 | 4/1969 | Blume | 210/656 |
| 3,511,377 | 5/1970 | Hrdina | 210/198.2 |
| 3,615,235 | 10/1971 | Hrdina | 210/198.2 X |
| 3,935,884 | 2/1976 | Hazelton | 141/80 |
| 3,966,609 | 6/1976 | Godbille et al. | 210/198.2 |
| 4,280,905 | 7/1981 | Gunkel et al. | 210/198.2 |
| 4,361,482 | 11/1982 | Teetz et al. | 210/198.2 |
| 4,451,365 | 5/1984 | Sättler | 210/198.2 |
| 4,483,374 | 11/1984 | Siemion | 141/9 |

OTHER PUBLICATIONS

*High Performance Liquid Chromatography* by Knox, Edit. Chpt. 12 pp. 147–156.

*Primary Examiner*—Stephen Marcus
*Assistant Examiner*—Ernest G. Cusick
*Attorney, Agent, or Firm*—Schwartz, Jeffery, Schwaab, Mack, Blumenthal & Evans

[57] ABSTRACT

A process and apparatus for filling and packing a chromatographic column by the wet route in which a compression chamber is attached to one end of the column having an internal bore equal to the internal diameter of the column and aligned therewith to form a combined chamber, a fluid suspension of packing particles is introduced into the combined chamber and then a piston member is axially displaced within the compression chamber toward the chromatographic column to compact the packing particles in the column. The suspension liquid flows out of the column through a conduit formed through the piston and/or through the cap at the other end of the column. After compression, the compression chamber and piston are separated from the column and the packed column may then be attached to a chromatograph for use. Vibrators may be provided on the column or compression chamber to promote transverse rearrangement of the particles during compression. The liquid suspension of packing particles may be introduced into the combined chamber via a channel through the piston, or through the compression chamber after removing the piston, or through the opposite end of the chromatographic column. A porous plate may be placed over the conduit to prevent packing particles from exiting the combined chamber with the suspension liquid.

18 Claims, 6 Drawing Figures

PROCESS AND DEVICE FOR FILLING CHROMATOGRAPHY COLUMNS

The present invention concerns a process and a device for filling chromatography columns that enables for said columns to attain performances close to the theoretical limit fixed by the packing characteristics, whatever the diameter of the column. It is especially suitable for fine granulometry packing (particles having a diameter smaller than 40 microns) that enables achievement of good efficiency.

Numerous processes have been described to fill the small diameter columns used in analytical chemistry with very low granulometry packing formed of grains presently comprised between 3 and 10 microns. All these processes use the flash expansion in the column of a suspension of the packing in a suitable liquid, the said column having been previously brought under high pressure (several hundred bars). This is the so called packing by the wet route that has the aim of obtaining as homogenous and compact packing as possible of the porous bed.

When the diameters of the columns are large, this method quickly becomes impracticable due to the technological restrictions that it imposes. For these columns, two packing processes are still used in liquid chromatography; they are known under the names of "radial compression" and "axial compression".

The radial compression process is a dry packing process and makes use of a column with a double envelope system. The internal envelope that constitutes the column per se is a cylinder made of deformable flexible material that contains the dry packing. The internal envelope is placed in the external envelope constituted by a rigid metallic cylinder. A gas pressure of 30 to 40 bars is applied in the sealed annular space comprised between the two cylinders, thus "radially" compressing the packing. The homogeneity and compactness of the packing are assumed to exist prior to the application of the pressure which only has the effect of preserving these when the column is eluted.

The axial compression process is a method of packing by the wet route. The column is constituted by a cylinder in which slides a piston, the assembly being carefully machined and adjusted. The piston, movable by a jack, enables compression of the packing put in suspension in a liquid in order to obtain the consolidation necessary to realize good performances. The column is thus constituted by the cylinder-piston-jack assembly and is maintained under pressure during elution.

These two processes have the drawback of imposing the utilisation of rather complex material and, above all, cumbersome maintenance of the static pressure during elution. Furthermore, they do not allow the rearrangement of the packing particles during compression, thus leading to the incomplete settling of the packing.

One of the objects of the present invention is to provide a system for packing the classical chromatographic columns, especially by the wet route that derives from the process called "axial compression process" but which is operated in a manner so as to use the columns without requiring special machining and allows the rearrangement of the particles during the compression.

With this purpose, the packing process of a chromatographic column, especially by the wet route, is characterized in that it consists in equipping the empty column with a compression chamber, in introducing into the single chamber formed by the column and the compression chamber a liquid in which the packing of the column is in suspension and in compacting it by the combination of an axial pressure applied to the packing, then in separating the chamber from the column, preferably by rotation of a composite junction element, and in mounting on the column its head mouthpiece or cap. When the packing down or settling is complete, the column is detached from the apparatus and can be used on any chromatography apparatus.

This system enables production of columns whose performances only depend upon the quality of the packing and are equal to the maximal performances predicted by theoretical considerations, regardless of the diameter of the column, from 1 to 100 centimetres. These performances expressed in reduced height of a theoretical plate correspond to a height approximately equal to 3 times the diameter of a particle.

The column and the compression chamber can be subjected to vibrations that are generated by mechanical means, by a source of fluid without pressure or by piezo-electric means, and which means act in the direction of their length or transversely to their axis. Preferably at least one vibration source is disposed at the periphery of the column and/or of the compression chamber and/or their junction-element at different levels.

The column thus obtained can be used independently on any chromatographic assembly and may comprise only the elements necessary to the maintenance of the packing and to the correct hydrodynamic flow of the eluent.

The device for operating the process that is described immediately above and which comprises a compression chamber put under pressure by means of a piston sliding in a sealed manner in a bore of the compression chamber and activated by a mechanical element, such as a jack rod, is characterized in that at least one filling conduit extends through the piston, and the exits of the compression chamber are adapted to be sealed by a valve. Preferably, the piston bears a collector separated from the inside of the compression chamber by a porous sheet or a grid and connected to an external discharge by a conduit adapted to be sealed by a valve.

Other aims, advantages and characteristics of the invention will appear from reading through the description of an embodiment of the invention, given by way of nonlimitative example and with respect to the accompanying drawings in which:

FIGS. 1 and 2 show that when an isotropic pressure is applied to a packing during compaction in the known devices certain grains of the packing (hatched on the figures) can be arranged in such a manner that they form stable cavities inside which no compaction occurs such as A.

Figure 1:
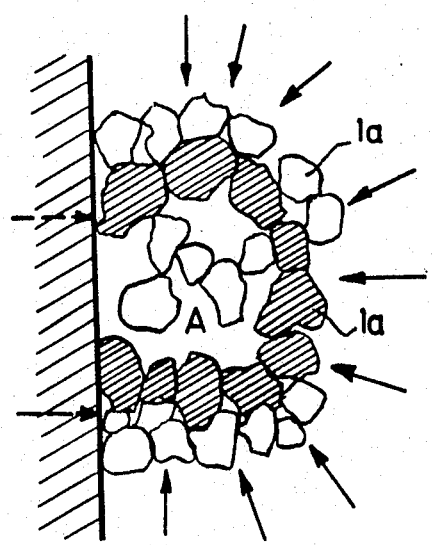
FIGS. 1 and 2 show schematically the results of the compressing or settling obtained on the packing of the chromatographic columns of a known type.
Figure 2:
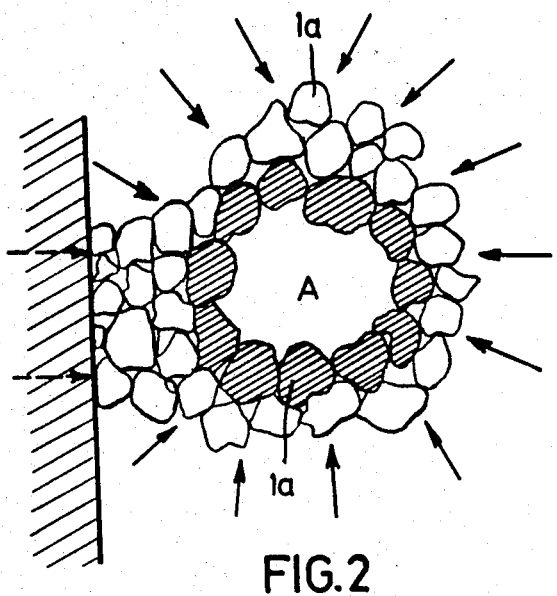
Figure 3:
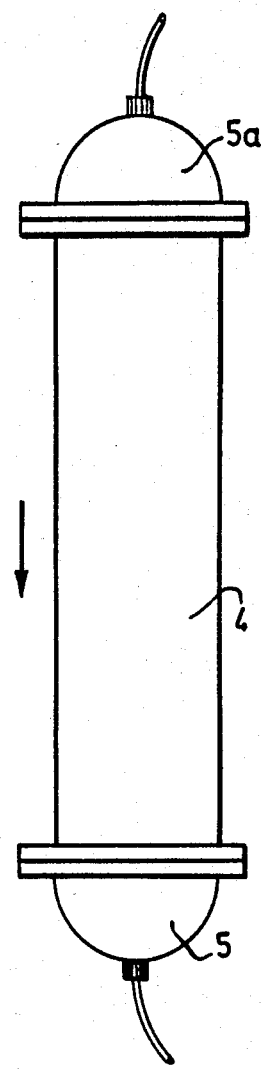
FIG. 3 represents a plane exterior view of a chromatography column, such as generally presented.

FIG. 3 shows a chromatographic column in the form of a cylinder 4 at the ends of which are fixed two parts called head 5a and bottom 5 end closures or caps of column 4.

Figure 4:
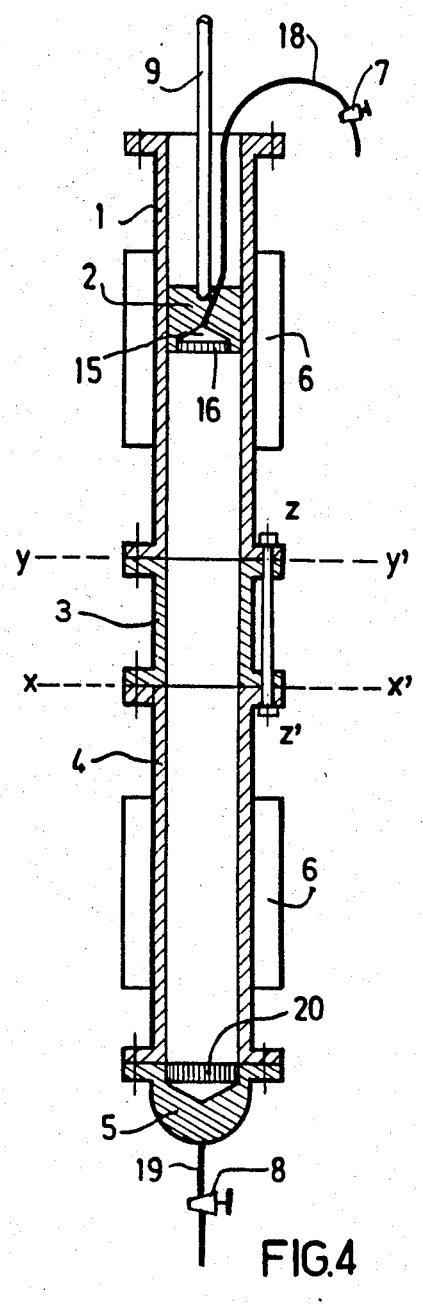
FIG. 4 represents in a schematic cross-section the apparatus for packing of a chromatography column according to the invention.

These caps or 1 end closures 5 and 5a comprise especially a porous sheet 20 that serves to retain the packing and allow the passage of the carrier liquid (see FIG. 4).

Figure 6:
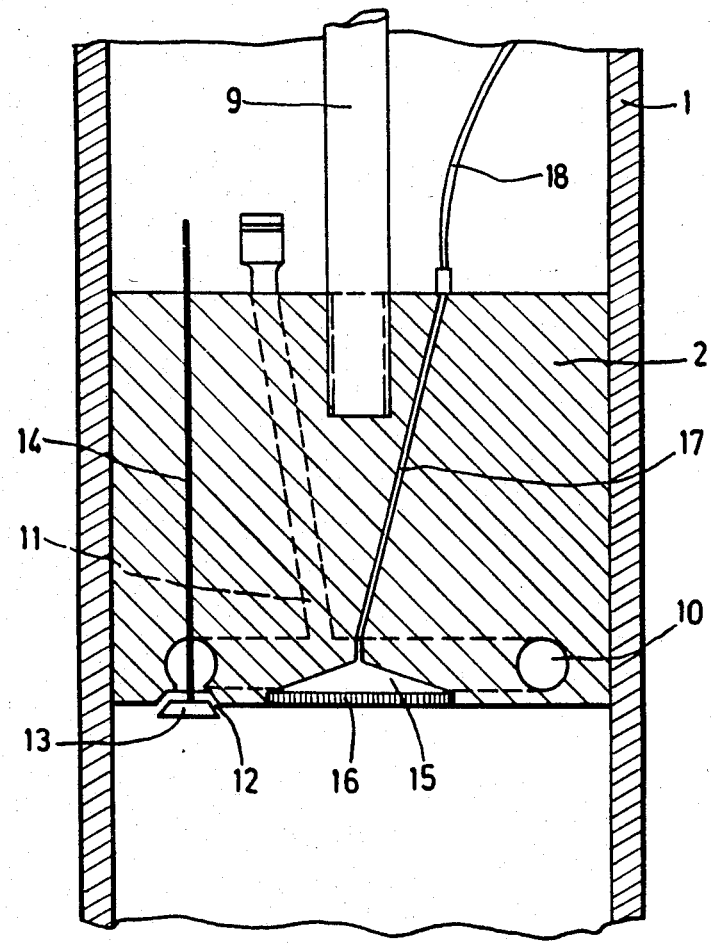
FIG. 6 is a cut-away cross section on larger scale of the compression chamber of the packing device at the level of the piston.

The packing system concerned in the present invention is represented FIG. 4 and is formed of four principal parts:

a cylindrical compression chamber 1, having an internal diameter identical to that of the columns, and provided with a cylindrical bore having good geometric and frictional qualities;

a piston 2 that can slide in a sealed manner in the bore of the chamber 1 and is carefully adjusted in this bore in such a way as to ensure excellent tightness. Piston 2 can be activated by a jack or any other mechanical device. Its front face that exerts the thrust in chamber 1 is hollowed out with a recess, forming collector 15, sealed by a porous sheet 16 and connected to an exterior receptacle by an intermediate flexible pipe-line 18 that can be closed by valve 7 (see FIG. 6).

a junction element 3 that solidly attaches chamber 1 and column 4 by means of bolted down flanges. This element can pivot about an axis zz' after having been loosened from the compression chamber 1 and the column 4.

elastic vibration emitters 6 that are fixed to the sides of chamber 1 and column 4. The vibration source(s) can be mechanically activated by liquid pressure or piezo-electric means.

In order to proceed with the packing of column 4, the column is fixed to a junction element 3 assembled to the compression chamber 1 and is equipped with its bottom cap or end closure 5 the exit pipe-line 19 of which is adapted to be sealed by a valve 8. Piston 2 is disengaged from the upper part of the compression chamber 1. Packing 1a is thus introduced in the form of a suspension in an appropriate liquid, into the common chamber formed inside chamber 1, junction element 3 and column 4 after valve 8 has been closed down. The vibration sources 6 are thus put into service; they contribute to the maintenance of the homogeneity of the suspension. Piston 2 is replaced in the bore of chamber 1 and urged towards the bottom by piston rod 9, the valve 7 being open. This allows the air trapped above the liquid suspension to escape towards the outside.

When the liquid appears beyond valve 7, the valve 8 is also opened while the piston continues its displacement towards cap 5. Packing becomes compact.

While the suspension fluid flows towards the outside, the vibrations promote the rearrangement of the particles. The volume of the suspension introduced has been calculated so that when optimal compactness is achieved, piston 2 is still in compression chamber 1, its thrust face being situated slightly above plane y y'. The flow towards the exterior stops, whereas the pressure in the system increases more rapidly. The jack rod 9 is blocked and the junction 3-column 4 assembly is loosened from compression chamber 1. Jack rod 9 is again urged towards cap 5 with care, having the effect of disengaging a plug of compacted packing that remains in the compression chamber 1. Thereafter the flanges opposite the junction element 3 and the column 4 that are only united by axis z-z' are loosened and the junction element 3 is caused to pivot about this axis 2-2'. The rib of the lower flange of junction element 3 divides up and levels off the porous bed at the upper part of the column 4. On the smooth surface obtained, the porous filter of the head cap 5a is thus perfectly applied without creation of dead volume. The column 4 is thus ready for use.

The principle of the invention thus consists in exerting simultaneously on the packing in suspension in a liquid contained in a chromatographic column, a force directed along the axis of this column and that imposes the settling movement and the elastic vibrations that promote transverse rearrangements of the particles. A column filled in a homogenous manner with a porous bed of optimal compactness is obtained.

Two other versions of this system have been realized and applied to filling of columns with various diameters.

Figure 5:
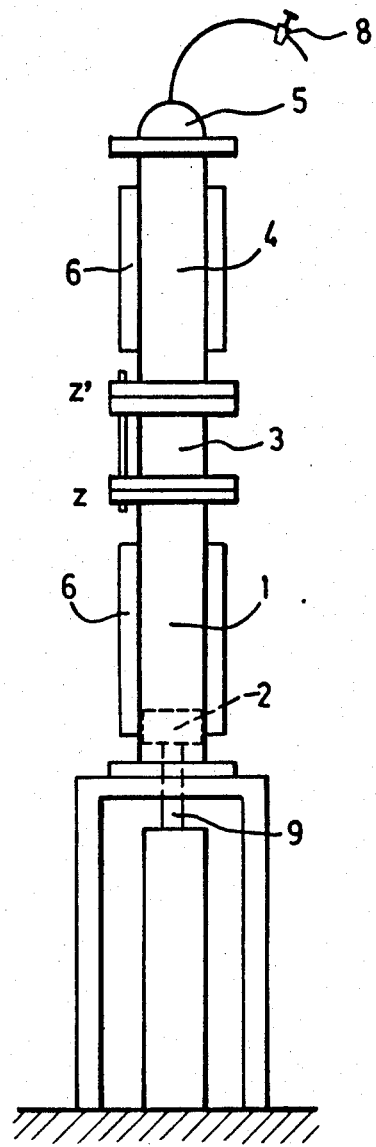
FIG. 5 represents a plane exterior view of the same packing device for a column having a smaller diameter.

For the columns having a small or medium diameter, the same principal elements are used: chamber 1-piston 2-junction element 3 -column 4 vertically placed above the thurst device 9 in the reverse order as shown in FIG. 5. To proceed with this filling, the piston 2 is displaced to its lowermost position and column 4 is opened by raising the cap 5 situated at the top. The suspension can thus be introduced and, after closing by replacing cap 5, the compacting operations described hereinabove can be carried out.

The junction element 3-column 4 assembly is thereafter detatched, vertically returned and the continuation of the process proceeds. It is thus not necessary to remove the piston 2 from the compression chamber 1.

For columns having a large diameter, the arrangement of the elements corresponds to that of FIG. 4 but piston 2 is provided with a feed device that also makes it possible to avoid extraction of the piston during filling of the chamber with the suspension. This mounting is represented in cross-section on FIG. 6, in a schematic manner. Piston 2 slides in the bore of compression chamber 1. It is activated by the thrust rod 9. A toric groove 10 machined in the body of piston 2 is connected to the upper face of said body by a conduit 11 and to the lower thrust face by an orifice 12 closed by a valve 13 at the end of an activating rod 14. A central collector 15 sealed by a porous sheet 16 is connected to the upper face by a conduit 17 leading to pipe-line 18 on which is disposed the valve 7.

Piston 2 being at the top of in the chamber, the filling of the system with the suspension is carried out through conduit 11, the groove 10 and orifices 12. These are thereafter sealed by valves 13 and the compacting is effected as described hereinabove.

The vibration operating means can be disposed either at the periphery of the column 4 and compression chamber 1 and in different positions along the axis of the cylindrical assembly that they form, or on a cap 5, 5a of the column on the connecting flanges of the different elements and on the fixation flange of the assembly to a frame, or by combining these two types of arrangement.

Furthermore, the performances obtained with a chromatographic column packed according to the invention are expressed in terms of the reduced height of a theoretical plate, i.e. by the numerical ratio h/dp of the height h of a theoretical plate to the average diameter dp of the particles of the packing. The system of the instant invention allows regular attainment of the value 3 for this ratio.

Of course, the present invention is not limited to the embodiments described and represented; it is adaptable to numerous variants available to the man skilled in the art, without departing from the spirit and the scope of the invention.

We claim:

1. Apparatus for filling and packing a chromatographic column having a defined bore, said apparatus comprising:
   a compression chamber having the same bore as said chromatographic column, said compression chamber being selectively attachable at and detachable from one end of said chromatographic column such that the interior of said compression chamber is aligned with the interior of said chromatographic column to form a combined chamber;
   a piston sealingly fitting in said compression chamber;
   means for selectively moving said piston in said compression chamber toward and away from said chromatographic column;
   means for closing the other end of said chromatographic column; and
   a conduit extending through at least one of said piston and said other end closing means through which a suspending liquid for packing particles for said chromatographic column may exit from said combined chamber 2. Apparatus according to claim 1, further comprising a porous member interposed across said conduit for preventing packing particles from exiting said combined chamber with said suspending liquid through said conduit.

3. Apparatus according to claim 1, wherein a junction element having the same bore as said chromatographic column and said compression chamber is interposed in alignment therebetween to form part of said combined chamber, said junction element being pivotable about an axis located outside of said combined chamber and extending parallel to the combined chamber.

4. Apparatus according to claim 1, further comprising vibrating means associated with at least one of said chromatographic column and said compression chamber for promoting transverse rearrangement of said packing particles during compression thereof.

5. Apparatus according to claim 1, wherein a filling channel is formed through said piston for introducing a suspension of packing particles into said combined chamber, and a valve is provided for selectively opening and closing said filling channel.

6. Apparatus according to claim 1, wherein both said piston and said other end closure means are provided with conduits through which suspending liquid may exit said combined chamber.

7. Apparatus according to claim 1, wherein a collector depression is formed on the inside face of said piston communicating with said conduit and covered by a porous sheet.

8. Apparatus according to claim 1, further comprising a valve for selectively opening and closing said conduit.

9. A process for filling a chromatographic column having a defined bore, said process comprising the steps of:
   attaching a compression chamber having a bore the same as the bore of the chromatographic column to be filled to one end of said chromatographic column in alignment therewith to form a combined chamber;
   filling said combined chamber with a suspension of packing particles in a suspending liquid;
   urging a piston sealingly disposed in the bore of said compression chamber axially toward said chromatographic column whereby said packing particles are compacted in said combined chamber and said suspending liquid is forced to exit said combined chamber through a conduit formed through at least one of said piston and means for closing the other end of said chromatographic column; and
   detaching said compression chamber and a piston from said chromatographic column.

10. A process according to claim 9, wherein said suspension is filled into said combined chamber through a filling channel formed through said piston, and said filling channel is thereafter closed by a valve.

11. A process according to claim 9, wherein said suspension is filled into said combined chamber through said other end of said chromatographic column after which said other end is closed by said other end closing means.

12. A process according to claim 9, further comprising the step of vibrating said combined chamber to promote transverse rearrangement of said packing particles as the piston is urged toward the chromtographic column and said packing particles are compacted.

13. A process according to claim 12, wherein said vibrating is effected by a piezoelectric vibrator associated with one of said chromatographic column and said compression chamber.

14. A process according to claim 12, wherein said vibrating is effected by a liquid pressure activated mechanical vibrator associated with one of said chromatographic column and said compression chamber.

15. A process according to claim 12, wherein said vibrating is effected by application of fluid pressure to the side of one of said chromatographic column and said compression chamber.

16. A process according to claim 9, further comprising the steps of attaching an end closure to said one end of said chromatographic column and connecting the column to a chromatograph.

17. A process according to claim 9, wherein said suspension is filled into said combined chamber by removing said piston from said compression chamber, introducing the liquid suspension of packing particles through said compression chamber, and thereafter replacing said piston in said compression chamber.

18. A process according to claim 9, further comprising the step of leveling off the top of the packing particles after compaction by pivoting a pivotable junction element interposed between said chromatographic column and said compression chamber.

* * * * *